United States Patent
Kline

(10) Patent No.: US 7,344,497 B2
(45) Date of Patent: Mar. 18, 2008

(54) NON-INVASIVE DEVICE AND METHOD FOR MEASURING THE CARDIAC OUTPUT OF A PATIENT

(75) Inventor: Jeffrey A. Kline, Charolotte, NC (US)

(73) Assignee: Charlotte-Mecklenburg Hospital, Charolotte, NC (US)

( * ) Notice: Subject to any disclaimer, the term of this patent is extended or adjusted under 35 U.S.C. 154(b) by 296 days.

(21) Appl. No.: 11/160,961

(22) Filed: Jul. 18, 2005

(65) Prior Publication Data
US 2005/0245833 A1    Nov. 3, 2005

Related U.S. Application Data

(62) Division of application No. 10/400,339, filed on Mar. 26, 2003, now Pat. No. 7,083,574.

(51) Int. Cl.
A61B 5/00 (2006.01)
A61B 5/02 (2006.01)
A61B 5/05 (2006.01)

(52) U.S. Cl. ............... 600/300; 600/526; 600/532; 600/529

(58) Field of Classification Search ............ None
See application file for complete search history.

(56) References Cited

U.S. PATENT DOCUMENTS 6,517,496 B1 * 2/2003 Mault .............. 600/532

2004/0186390 A1 * 9/2004 Ross et al. .............. 600/532
2005/0177046 A1 * 8/2005 Mills .............. 600/481

FOREIGN PATENT DOCUMENTS

| JP | 57-180942 | 11/1982 |
|---|---|---|
| JP | 57-206425 | 12/1982 |
| JP | 58-19235 | 2/1983 |
| JP | 60-227733 | 11/1985 |
| JP | 5-337102 | 12/1993 |
| JP | 5-509026 | 12/1993 |
| JP | 2000-37368 | 2/2000 |
| JP | 2001-516255 | 9/2001 |
| WO | WO 00/50890 | 8/2000 |
| WO | WO 00/67643 A3 | 11/2000 |

* cited by examiner

*Primary Examiner*—Robert L Nasser
(74) *Attorney, Agent, or Firm*—George R. McGuire; Bond Schoeneck & King, PLLC

(57) ABSTRACT

The invention involves a device and method for ascertaining the functioning of the respiratory system and, in particular, determining the cardiac output of a patient. The device comprises an apparatus containing sensors for measuring the oxygen and carbon dioxide concentrations as well as the volume of air inhaled and exhaled by a patient. The patient is provided a mouthpiece for breathing into and out of the device, which subsequently measures oxygen partial pressures of the inhaled and exhaled air. In addition, the patient's arterial oxygen saturation is continuously measured through pulse oximetry and the pH and hemoglobin concentration is determined from a venous blood sample. From this data, the cardiac output of the patient may be calculated.

8 Claims, 3 Drawing Sheets

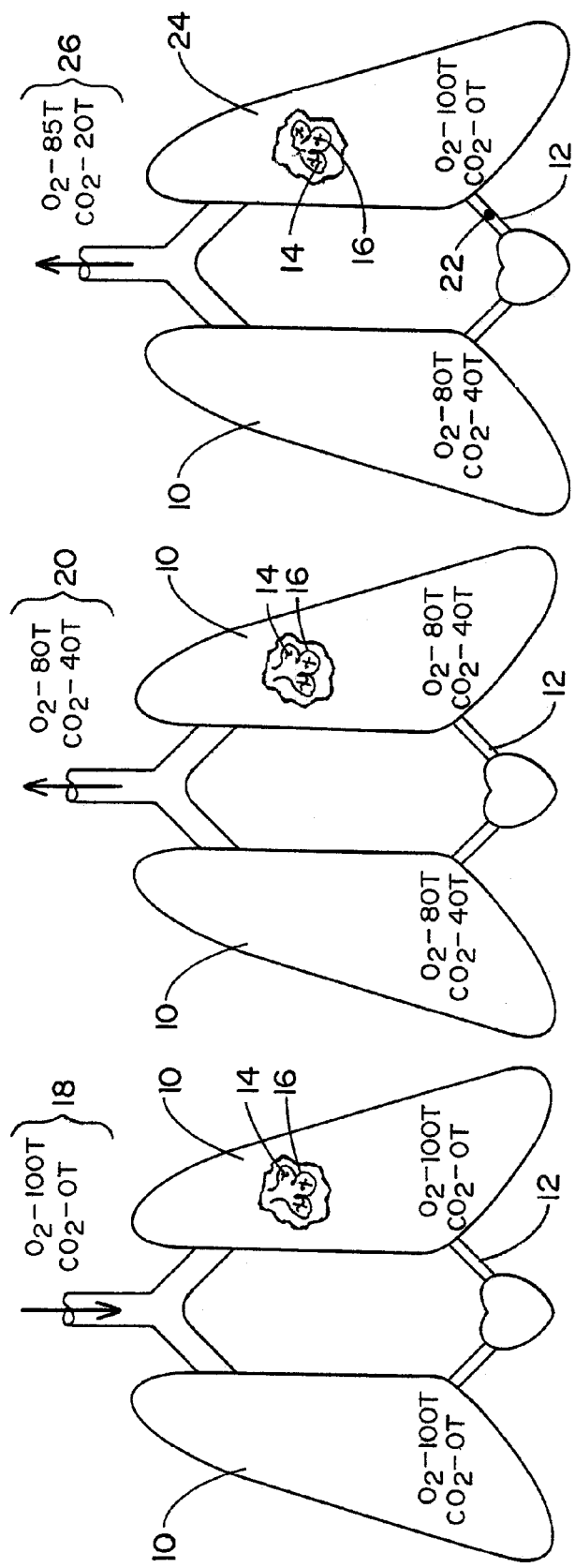

NON-INVASIVE DEVICE AND METHOD FOR MEASURING THE CARDIAC OUTPUT OF A PATIENT

CROSS REFERENCES TO RELATED APPLICATION

The present application is a divisional of Applicant's co-pending U.S. application Ser. No. 10/400,339, filed on Mar. 26, 2003, which is a divisional application of U.S. Pat. No. 6,575,918, filed on Sep. 27, 2001.

BACKGROUND OF THE INVENTION

1. Field of Invention

The present invention relates generally to improvements in technology used in the field of vascular occlusions of the respiratory system, and more particularly to non-invasive devices and methods for the diagnosis of a pulmonary embolism and related disorders.

2. Description of Prior Art

A pulmonary embolism occurs when an embolus becomes lodged in lung arteries, thus blocking blood flow to lung tissue. An embolus is usually a blood clot, known as a thrombus, but may also comprise fat, amniotic fluid, bone marrow, tumor fragments, or even air bubbles that block a blood vessel. Unless treated promptly, a pulmonary embolism can be fatal. In the United States alone, around 600,000 cases occur annually, 10 percent of which result in death.

The detection of a pulmonary embolism is extremely difficult because signs and symptoms can easily be attributed to other conditions and symptoms may vary depending on the severity of the occurrence. Frequently, a pulmonary embolism is confused with a heart attack, pneumonia, hyperventilation, congestive heart failure or a panic attack. In other cases, there may be no symptoms at all.

Often, a physician must first eliminate the possibility of other lung diseases before determining that the symptoms, if any, are caused by a pulmonary embolism. Traditional diagnostic methods of testing involve blood tests, chest X-rays, and electrocardiograms. These methods are typically more effective in ruling out other possible reasons than for actually diagnosing a pulmonary embolism. For example, a chest x-ray may reveal subtle changes in the blood vessel patterns after an embolism and signs of pulmonary infarction. However, chest x-rays often show normal lungs even when an embolism is present, and even when the x-rays show abnormalities they rarely confirm a pulmonary embolism. Similarly, an electrocardiogram may show abnormalities, but it is only useful in establishing the possibility of a pulmonary embolism.

As a pulmonary embolism alters the ability of the lungs to oxygenate the blood and to remove carbon dioxide from the blood, one method of diagnosing the condition involves taking a specimen of arterial blood and measuring the partial pressure of oxygen and carbon dioxide in the arterial blood (i.e., an arterial blood gas analysis). Although a pulmonary embolism usually causes abnormalities in these measurements, there is no individual finding or combination of findings from the arterial blood gas analysis that allows either a reliable way to exclude or specific way of diagnosing pulmonary embolism. In particular, at least 15-20% of patients with a documented pulmonary embolism have normal oxygen and carbon dioxide contents of the arterial blood. Accordingly, the arterial blood gas analysis cannot reliably include or exclude the diagnosis of a pulmonary embolism.

The blood D-dimer assay is another diagnostic method that has become available for commercial use. The D-dimer protein fragment is formed when fibrin is cleaved by plasmin and therefore produced naturally whenever clots form in the body. As a result, the D-dimer assay is extremely sensitive for the presence of a pulmonary embolism but is very nonspecific. In other words, if the D-dimer assay is normal, the clinician has a reasonably high degree of certainty that no pulmonary embolism is present. However, many studies have shown a D-dimer assay is only normal in less than ⅓ of patients and thus produces a high degree of false positives. As a result, the D-dimer assay does not obviate formal pulmonary vascular imaging in most patients with symptoms of a pulmonary embolism.

In an attempt to increase the accuracy of diagnostic, physicians have recently turned to methods which can produce an image of a potentially afflicted lung. One such method is a nuclear perfusion study which involves the injection of a small amount of radioactive particles into a vein. The radioactive particles then travel to the lungs where they highlight the perfusion of blood in the lung based upon whether they can penetrate a given area of the lung. While normal results can indicate that a patient lacks a pulmonary embolism, an abnormal scan does not necessarily mean that a pulmonary embolism is present. Nuclear perfusion is often performed in conjunction with a lung ventilation scan to optimize results.

During a lung ventilation scan, the patient inhales a gaseous radioactive material. The radioactive material becomes distributed throughout the lung's small air sacs, known as alveoli, and can be imaged. By comparing this scan to the blood supply depicted in the perfusion scan, a physician may be able to determine whether the person has a pulmonary embolism based upon areas that show normal ventilation but lack sufficient perfusion. Nevertheless, a perfusion scan does not always provide clear evidence that a pulmonary embolism is the cause of the problem as it often yields indeterminate results in as many as 70% of patients.

Pulmonary angiograms are popular means of diagnosing a pulmonary embolism, but the procedure poses some risks and is more uncomfortable than other tests. During a pulmonary angiogram, a catheter is threaded into the pulmonary artery so that iodine dye can be injected into the bloodstream. The dye flows into the regions of the lung and is imaged using x-ray technology, which would indicate a pulmonary embolism as a blockage of flow in an artery. Pulmonary angiograms are more useful in diagnosing a pulmonary embolism than some of the other traditional methods, but often present health risks and can be expensive. Although frequently recommended by experts, few physicians and patients are willing to undergo such an invasive procedure.

Spiral volumetric computed tomography is another diagnostic tool that has recently been proposed as a less invasive test which can deliver more accurate results. The procedure's reported sensitivity has varied widely, however, and it may only be useful for diagnosing an embolism in central pulmonary arteries as it is relatively insensitive to clots in more remote regions of the lungs.

These pulmonary vascular imaging tests have several disadvantages in common. Nearly all require ionizing radiation and invasiveness of, at a minimum, an intravenous catheter. The imaging tests also typically involve costs of more than $1,000 for the patient, take more than two hours to perform, and require special expertise such as a trained technician to perform the tests and acquire the images and a board-certified radiologist to interpret the images. Notably, none are completely safe for patients who are pregnant. As a result of these shortcomings, the imaging procedures are not available in many outpatient clinic settings and in many portions of third world countries.

OBJECTS AND ADVANTAGES

It is a principal object and advantage of the present invention to provide physicians with an instrument for non-invasively diagnosing pulmonary vascular occlusions.

It is an additional object and advantage of the present invention to provide physicians with an instrument that accurately diagnoses pulmonary vascular occlusions.

It is a further object and advantage of the present invention to provide an instrument for measuring and interpreting pulmonary test data.

Other objects and advantages of the present invention will in part be obvious, and in part appear hereinafter.

SUMMARY OF THE INVENTION

In accordance with the foregoing objects and advantages, the present invention provides a device and method for non-invasively diagnosing a pulmonary embolism. The device of the present invention comprises a breathing tube having sensors for measuring the flow of air into and out of a patient's lungs while a remote data processing unit interconnected to the breathing tube simultaneously determines the oxygen and carbon dioxide concentrations. The device further includes a display screen for visually graphing the resulting calculations and providing a visual means for determining the likelihood that a pulmonary embolism is present based upon a change in measured gas concentrations.

BRIEF DESCRIPTION OF THE DRAWINGS

FIG. 1 is an illustration of a respiratory system during inhalation.

FIG. 2 is an illustration of a respiratory system during exhalation.

FIG. 3 is an illustration of a respiratory system afflicted with a pulmonary vascular occlusion during exhalation.

DETAILED DESCRIPTION

Figure 4:
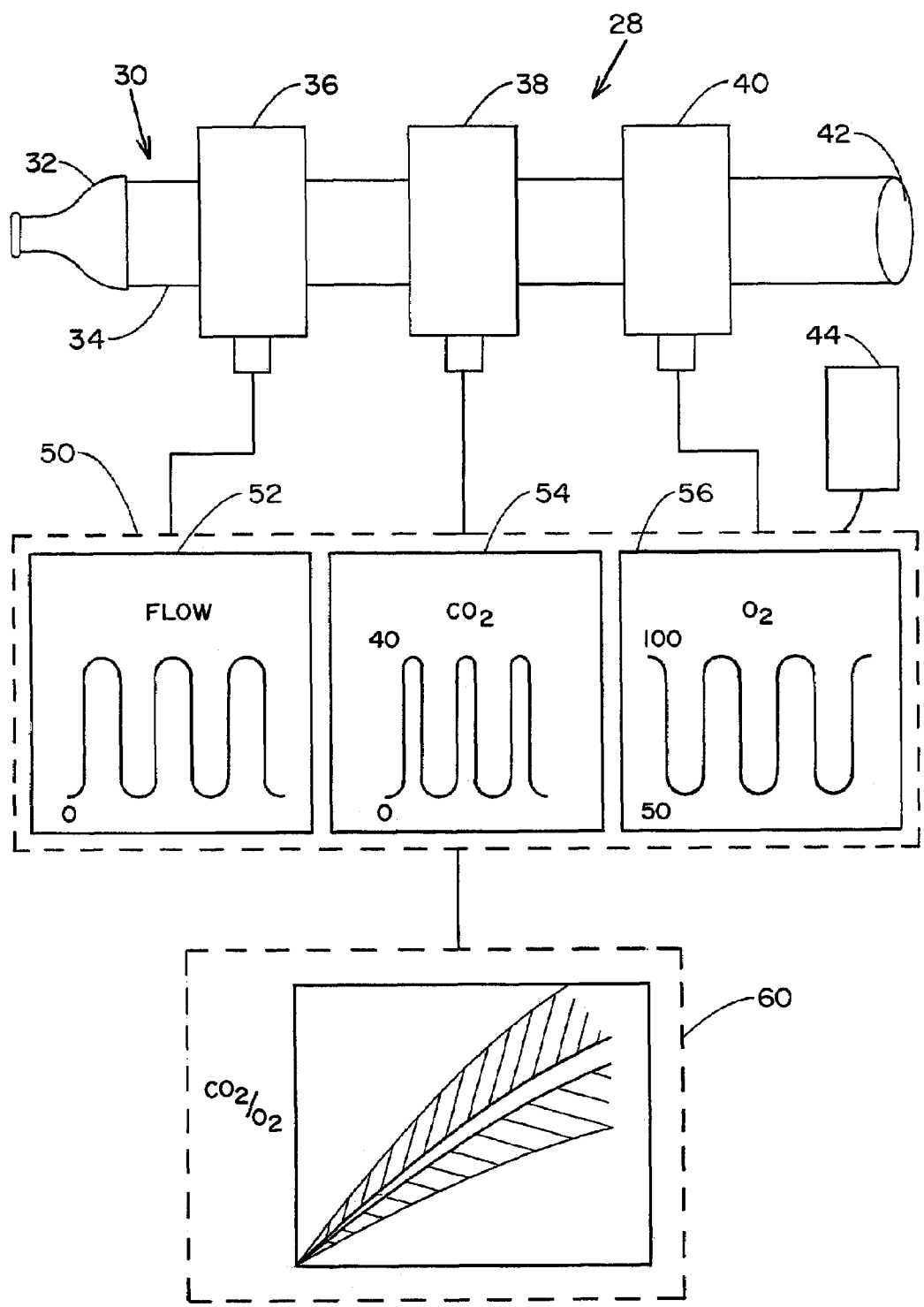
FIG. 4 is a schematic representation of the system of the present invention.

Referring now to the drawing in which like reference numerals refer to like parts throughout, there is seen in FIG. 1 a representation of lungs 10 free from any pulmonary occlusions. In healthy lungs 10, blood flows freely from the pulmonary arteries 12 into the capillaries 14 surrounding the individual alveoli 16 of the lungs 10. When inhaled air 18 is drawn into the lungs 10 and alveoli 16, oxygen is transferred from the inhaled air 18 to the blood stream and carbon dioxide is transferred out. Inhaled air 18 typically contains an oxygen partial pressure of approximately one hundred (100) torr and a carbon dioxide partial pressure of zero (0) torr.

Once the inhaled air 18 reaches the alveoli 16, the oxygen content decreases while the carbon dioxide content increases until an equilibrium with blood gas levels in the pulmonary arteries 12 is reached. The inhaled air 18 is then, as seen in FIG. 2, expired as exhaled air 20. Exhaled air 20 from properly functioning lungs typically contains a partial pressure of oxygen of about eighty (80) torr and a partial pressure of carbon dioxide of about forty (40) torr.

FIG. 3 depicts the functioning of a respiratory system afflicted with a pulmonary embolism 22 which, as an example, occludes blood flow to an afflicted lung 24. As a result, there is a reduction in the number of alveoli 16 that participate in gas exchange. This volume of space available in the alveoli 16 that is lost from participation is commonly referred to as alveolar deadspace. Due to the deadspace and loss of total alveolar volume available for gas exchange, afflicted lung 24 does not exchange gases as readily as the healthy lung 10. Accordingly, exhaled air 26 contains a higher partial pressure of oxygen and lower partial pressure of carbon dioxide than air exhaled from a healthy lung. In the example depicted in FIG. 3, exhaled air 26 exiting the respiratory system contains a partial pressure of oxygen of about eighty-five (85) torr and a partial pressure of carbon dioxide of about twenty (20) torr. Thus, the ratio of carbon dioxide to oxygen in exhaled air 26 from afflicted lung 24 (i.e., 20:85) is smaller than the ratio in exhaled air 20 from healthy lung 10 (i.e., 40:80) as seen in FIG. 2.

As seen in FIG. 4, a system 28 for measuring and diagnosing pulmonary disorders comprises a measuring unit 30 in combination with a data processing unit 50 and a display screen 60. Measuring unit 30 determines the overall flow of air inhaled into and exhaled out of the lungs while simultaneously determining the partial pressure of oxygen and carbon dioxide. Data processing unit 50 computes the concentrations of carbon dioxide, oxygen, and nitrogen from the partial pressures and determines the ratio of carbon dioxide to oxygen from the raw data obtained by measuring unit 30. The ratio of carbon dioxide to oxygen is then plotted against expired volume on display screen 60. By comparing the carbon dioxide ratios to average readings, the likelihood that a given patient has a pulmonary embolism can be determined.

Measuring unit 30 comprises a patient mouthpiece 32 connected in fluid communication to a breathing tube 34 having an open end 42 through which air can be inhaled or exhaled. Measuring unit 30 further comprises three sensors; a pneumotach 36, a capnometer 38, and an oxygen monitor 40. The three sensors are situated in series and in-line with breathing tube 34 for simultaneously measuring the flow, carbon dioxide, and oxygen levels of inhaled and exhaled air. Infrared and paramagnetic type sensors are preferred respectively. Sensors using spectrometric techniques may also work for both oxygen and carbon dioxide measurements providing they can supply data with rapid enough response time for breath-to-breath, real-time plotting. The mainstream technique for measuring the inhaled or exhaled air is preferred, but the sidestream technique may also be effective.

Figure 5:
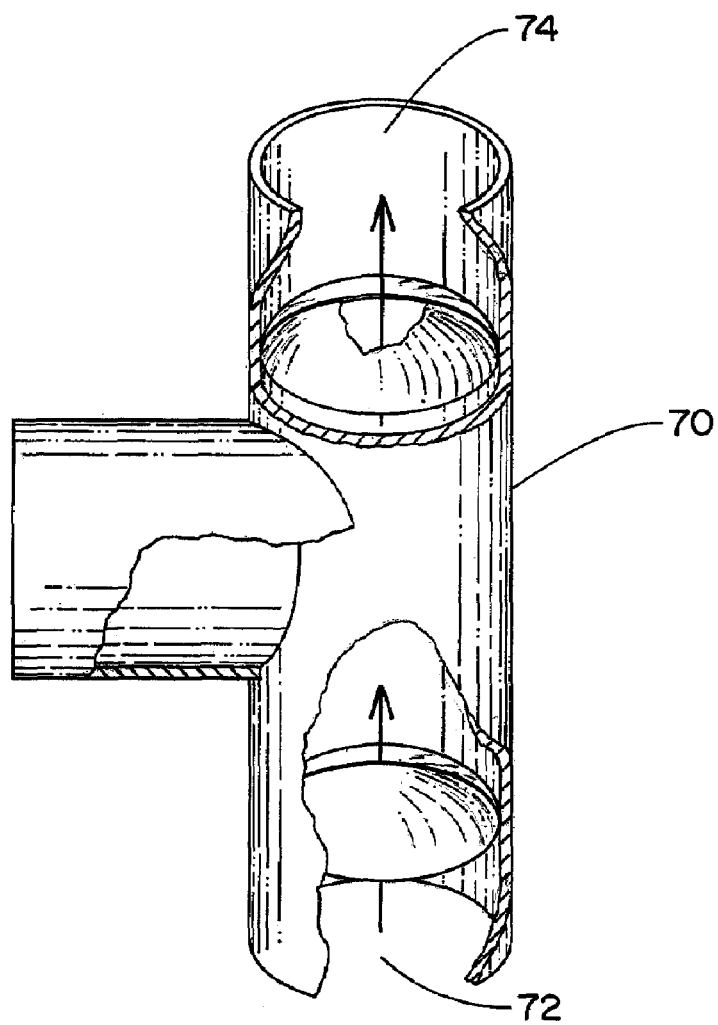
FIG. 5 is a perspective view of an attachment to the invention.

As seen in FIG. 5, a T-piece adaptor 70 may optionally be provided at open end 42 of breathing tube 34 for use with patients that are oxygen dependant. T-piece adapter 70 contains an inlet valve 72 and an outlet valve 74 which properly direct the passage of inhaled and exhaled air through the breathing tube 34. By connecting an oxygen dependant patient's supply to the intake valve 72, inhaled air can first be passed through the three sensors 36, 38, 40 to establish baseline readings of the oxygen and carbon dioxide concentrations for comparison to exhaled air, since an oxygen dependent patient receives air that has different concentrations than present in ambient air.

Data processing unit 50 comprises a commercially available computer processor programmed with software for the interpretation of the data obtained from measuring unit 30 and background comparison data. Software can be specifically developed to perform the necessary calculations to determine the partial pressures and carbon dioxide to oxygen ratios or software can optionally be purchased commercially and, if necessary, modified to run the appropriate algorithms. After additional research, the background comparison data can be updated based on data obtained from use of the invention to further refine expected normal values.

Display screen 60 comprises a cathode ray tube, plasma screen, or other visual display for displaying computerized data. Screen 60 can optionally display graphs representing predetermined reference or background data for test populations against which the current readings can be plotted for a visual comparison. In addition to displaying the carbon dioxide to oxygen ratios as a function of time calculated by data processing unit 50, screen 60 may optionally display a plot of the expired oxygen and carbon dioxide partial pressures. Using this display, a physician may estimate the efficiency of alveolar ventilation in patients with acute respiratory distress syndromes to assist in deciding the mechanical ventilation settings.

In addition to the three primary sensors 36, 38, 40, data processing unit 50 may optionally be connected to a pulse oximeter 44 that measures arterial oxygen saturation of hemoglobin in the arterial blood. From these data, and the additional measurement of pH and hemoglobin concentration in a peripheral venous blood sample, the cardiac output of the patient can be calculated according to the Fick equation. In order to perform the Fick equation, the average total oxygen consumed, the arterial oxygen content and venous oxygen content must be determined. The average total oxygen consumed can be determined from the oxygen tension and flow curves over a predetermined time period. For the purposes of determining cardiac output, a one minute time period is sufficient. The arterial oxygen content can be estimated by multiplying the arterial oxygen saturation (measured by pulse oximeter 44) by the hemoglobin concentration (determined from the venous blood sample). The venous oxygen content can be calculated by mathematical manipulation of the nadir (mean lowest) oxygen tension measured during deep expiration (in an awake patient) or a sign exhalation (in a mechanically ventilated patient) over the predetermined time period. From the nadir oxygen tension, venous oxygen saturation can be estimated according to published oxygen binding curves for the measured pH. The venous oxygen content is then calculated by multiplying the venous oxygen saturation by the venous hemoglobin (measured from the venous blood sample). Once these calculations have been made, the cardiac output is determined by dividing the total oxygen consumed by the difference between the arterial oxygen content and the venous oxygen content. The algorithm for the Fick calculation can be programmed into the data processing unit software and the results displayed on screen 60. The cardiac output measurement is useful for assisting the physician in determining the success or failure of treatment designed to relieve pulmonary vascular obstructions, or to treat circulatory shock.

Device 28 is used by having a patient breathe (inhale and exhale a predetermined number of times in succession) through mouthpiece 32 of the measuring unit 30. As the patient inhales and exhales the pneumotach flow sensor 36, capnometer 38, and oxygen monitor 40 perform their respective readings, which are then electrically transmitted via wires or cabling to data processing unit 50. The programmable software loaded into data processing unit 50 convert the measurements into volume and concentration readings, calculate the carbon dioxide to oxygen ratio, and display this ratio on screen 60 in the form of a graph against the volume of air expired. Readings may be optimized by requiring the patient to hold in inhaled air for several heartbeats before exhaling through the mouthpiece 32 of the measuring unit 30. It has been determined through testing that patients without a pulmonary embolism will normally have a carbon dioxide to oxygen ratio of 0.30 or greater while patients with a pulmonary embolism will have a carbon dioxide to oxygen ratio of 0.25 or less.

Figure 6:
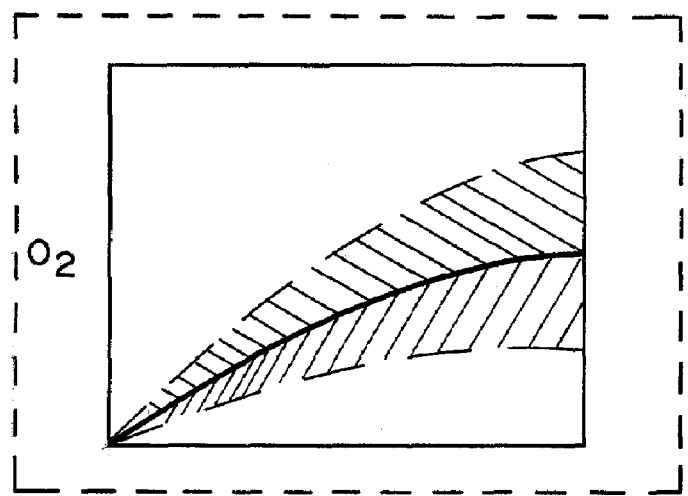
FIG. 6 is an illustration of a display screen readout.

Device 28 may also be used for the detection of whole-body oxygen consumption and determination of the adequacy of oxygen delivery during resuscitation from shock. During conditions of systemic inflammation the body will extract oxygen at higher levels than normal, resulting in an increase in the partial pressure of carbon dioxide-to-oxygen ratio in exhaled air. By using T-piece 70 in the manner explained above, the concentration of the oxygen provided to the patient and the concentration of the oxygen exhaled can be determined. As illustrated in FIG. 6, when the level of oxygen delivery (i.e., the amount provided minus the amount exhaled) observed at two inspired oxygen concentrations reaches normal levels a physician has visual conformation that the resuscitation performed is adequate. One method of determining the adequacy of resuscitation is to determine oxygen delivery at both relatively low fixed concentrations of oxygen and at relatively high fixed concentration. Relatively low concentrations include from about twenty-one to thirty percent (21-30%) oxygen and relatively high oxygen concentrations involve about forty-five to one hundred percent (45-100%) oxygen. The difference between oxygen delivery at relatively low concentrations verses relatively high concentrations can be compared against a nomogram for healthy patients of similar age, body mass, body mass index, and gender and used to assess the adequacy of fluid and vasopressor resuscitation.

Data processing unit 50 can additionally be programmed to display on screen 60 any of the individual measurements taken by sensors 36, 38, 40, and 44, or combinations thereof for diagnostic purposes. For example, a plot of the expired carbon dioxide and oxygen concentration over time could be used to estimate the efficiency of alveolar ventilation in patients with acute respiratory distress syndrome. Additionally, the plotted data from sensors 36, 38, 40, and 44 could be used to assist in deciding how to properly adjust mechanical ventilators setting, such as the degree of positive end-expiratory pressure, minute ventilation, and peak inspiratory pressure settings, to optimize patient care. For example, data from sensors 36, 37, 40, and 44, can be plotted individually in patients who are being mechanically ventilated. By simultaneously plotting the partial pressures of oxygen and carbon dioxide as a function of volume of each breath, the amount of carbon dioxide released and percentage of oxygen extracted can be determined. If the barometric pressure is known or inputted into data processing unit 50, the efficiency of alveolar ventilation during each tidal volume breath can be calculated. This information can then be used to adjust mechanical ventilation to optimize alveolar efficiency or breathing alveolar ventilation efficiency.

What is claimed is:

1. A method of measuring the cardiac output of a patient, comprising the steps of:
   providing a mouthpiece to a patient;
   allowing said patient to inhale and exhale through said mouthpiece;
   continuously measuring oxygen partial pressures of the inhaled and exhaled air;
   continuously measuring the arterial oxygen saturation through pulse oximetry;
   measuring the pH and hemoglobin concentration of a venous blood sample taken from said patient; and
   calculating the cardiac output.

2. The method of claim 1, wherein the step of calculating the cardiac output further comprises the steps of:
   calculating the average total oxygen consumed over a predetermined time period;
   calculating the arterial oxygen content as the product of measured arterial oxygen saturation and hemoglobin concentration;
   determining the lowest mean oxygen tension during expiration over the predetermined time period;
   estimating the venous oxygen saturation from the mean lowest oxygen tension according to published oxygen binding curves for the measured pH;
   calculating the venous oxygen content as the product of venous oxygen saturation and the measured hemoglobin concentration; and
   dividing the average total oxygen consumed by the difference between the arterial oxygen content and venous oxygen content.

3. The method of claim 2, further comprising the step of displaying said cardiac output on a screen.

4. The method of claim 3, wherein said predetermined time period is about one minute.

5. The method of claim 3, wherein said arterial oxygen saturation is measured by a pulse oximeter.

6. The method of claim 3, wherein the oxygen partial pressures of said inhaled and exhaled air are measured by an oxygen monitor in fluid communication with said breathing tube.

7. The method of claim 3, wherein the carbon dioxide partial pressures of said inhaled and exhaled air are measured by a capnometer in fluid communication with said breathing tube.

8. The method of claim 1, wherein said step of calculating the cardiac output is performed by a data processor programmed to calculate the Fick equation.

* * * * *